US009517133B2

(12) United States Patent
George et al.

(10) Patent No.: US 9,517,133 B2
(45) Date of Patent: *Dec. 13, 2016

(54) MALLEABLE PROSTHESIS WITH ENHANCED CONCEALABILITY

(71) Applicant: Boston Scientific Scimed, Inc., Maple Grove, MN (US)

(72) Inventors: Stephanie A. George, St. Louis Park, MN (US); Sara Elizabeth Nelson, Plymouth, MN (US); Randall P. Rowland, Eden Prairie, MN (US); Charles C. Kuyava, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/540,761

(22) Filed: Nov. 13, 2014

(65) Prior Publication Data

US 2015/0073208 A1    Mar. 12, 2015

Related U.S. Application Data

(63) Continuation of application No. 12/256,829, filed on Oct. 23, 2008, now Pat. No. 8,911,350.
(Continued)

(51) Int. Cl.
*A61F 2/26* (2006.01)
*A61F 5/41* (2006.01)
*A61H 19/00* (2006.01)

(52) U.S. Cl.
CPC . *A61F 2/26* (2013.01); *A61F 5/41* (2013.01); *A61F 2005/411* (2013.01);
(Continued)

(58) Field of Classification Search
CPC ........ A61F 2/26; A61F 5/41; A61F 2005/411; A61F 2005/415; A61F 2005/417; H01B 12/10; H01B 7/1895; A61H 19/44
See application file for complete search history.

(56) References Cited

U.S. PATENT DOCUMENTS 2,268,321 A    11/1940    Flynn
3,832,996 A    9/1974    Kalnberz
(Continued)

FOREIGN PATENT DOCUMENTS

DE    2537506 A1    8/1975
EP    0051420 A1    5/1982
(Continued)

OTHER PUBLICATIONS

Abouassaly, R. et al., "Antibiotic-coated medical devices: with an emphasis on inflatable penile prosthesis", Asian J Androl. Sep. 2004; 6: 249-57.
(Continued)

*Primary Examiner* — Andrew Iwamaye
(74) *Attorney, Agent, or Firm* — Brake Hughes Bellermann LLP

(57) ABSTRACT

A malleable penile prosthetic device for implantation within a penis of a user includes a columnar body and a plurality of malleable cores within the columnar body. The columnar body has a proximal end, a distal end, and a central axis extending from the proximal end to the distal end. Each of the plurality of malleable cores extends along the central axis, is angularly displaced about the central axis from neighboring malleable cores, and includes a bundle of wires surrounded by a sleeve.

11 Claims, 3 Drawing Sheets

Related U.S. Application Data

(60) Provisional application No. 60/981,844, filed on Oct. 23, 2007.

(52) U.S. Cl.
CPC ............ *A61F 2230/0006* (2013.01); *A61F 2230/0069* (2013.01); *A61F 2250/0006* (2013.01); *A61F 2250/0018* (2013.01); *A61F 2250/0029* (2013.01); *A61F 2250/0032* (2013.01); *A61H 19/44* (2013.01)

(56) References Cited

U.S. PATENT DOCUMENTS

| | | | |
|---|---|---|---|
| 3,853,122 A | 12/1974 | Strauch et al. | |
| 3,893,456 A | 7/1975 | Small et al. | |
| 3,954,102 A | 5/1976 | Buuck | |
| 3,987,789 A | 10/1976 | Timm et al. | |
| 3,991,752 A | 11/1976 | Gerow | |
| 4,009,711 A | 3/1977 | Uson | |
| 4,066,073 A | 1/1978 | Finney et al. | |
| 4,151,840 A | 5/1979 | Barrington | |
| 4,151,841 A | 5/1979 | Barrington | |
| 4,177,805 A | 12/1979 | Tudoriu | |
| 4,187,839 A | 2/1980 | Nuwayser et al. | |
| 4,201,202 A | 5/1980 | Finney et al. | |
| 4,204,530 A | 5/1980 | Finney | |
| 4,222,377 A | 9/1980 | Burton | |
| 4,224,934 A | 9/1980 | Scott et al. | |
| 4,235,227 A | 11/1980 | Yamanaka | |
| 4,244,370 A | 1/1981 | Furlow et al. | |
| 4,267,829 A | 5/1981 | Burton et al. | |
| 4,318,396 A | 3/1982 | Finney | |
| 4,342,308 A | 8/1982 | Trick | |
| 4,345,339 A | 8/1982 | Muller et al. | |
| 4,353,360 A | 10/1982 | Finney et al. | |
| 4,360,010 A | 11/1982 | Finney | |
| 4,364,379 A | 12/1982 | Finney | |
| 4,369,771 A | 1/1983 | Trick | |
| 4,378,792 A | 4/1983 | Finney | |
| 4,383,525 A | 5/1983 | Scott et al. | |
| 4,392,562 A | 7/1983 | Burton et al. | |
| 4,399,811 A | 8/1983 | Finney et al. | |
| 4,399,812 A | 8/1983 | Whitehead | |
| 4,404,968 A | 9/1983 | Evans, Sr. | |
| 4,407,278 A | 10/1983 | Burton et al. | |
| 4,411,260 A | 10/1983 | Koss | |
| 4,411,261 A | 10/1983 | Finney | |
| 4,412,530 A | 11/1983 | Burton | |
| 4,424,807 A | 1/1984 | Evans, Sr. | |
| 4,441,491 A | 4/1984 | Evans, Sr. | |
| 4,449,520 A | 5/1984 | Palomar et al. | |
| 4,457,335 A | 7/1984 | Trick | |
| 4,483,331 A | 11/1984 | Trick | |
| 4,517,967 A | 5/1985 | Timm et al. | |
| 4,522,198 A | 6/1985 | Timm et al. | |
| 4,523,584 A | 6/1985 | Yachia et al. | |
| 4,532,920 A | 8/1985 | Finney | |
| 4,541,420 A | 9/1985 | Timm et al. | |
| 4,545,081 A | 10/1985 | Nestor et al. | |
| 4,550,719 A | 11/1985 | Finney et al. | |
| 4,550,720 A | 11/1985 | Trick | |
| 4,558,693 A | 12/1985 | Lash et al. | |
| 4,559,931 A | 12/1985 | Fischell | |
| 4,566,446 A | 1/1986 | Fogarty | |
| 4,572,168 A | 2/1986 | Fischell | |
| 4,574,792 A | 3/1986 | Trick | |
| 4,590,927 A | 5/1986 | Porter et al. | |
| 4,594,998 A | 6/1986 | Porter et al. | |
| 4,596,242 A | 6/1986 | Fischell | |
| 4,602,625 A | 7/1986 | Yachia et al. | |
| 4,604,994 A | 8/1986 | Sealfon | |
| 4,611,584 A | 9/1986 | Finney | |
| 4,619,251 A | 10/1986 | Helms et al. | |
| 4,622,958 A | 11/1986 | Finney | |
| 4,651,721 A | 3/1987 | Mikulich et al. | |
| 4,653,485 A | 3/1987 | Fishell | |
| 4,664,100 A | 5/1987 | Rudloff | |
| 4,665,902 A | 5/1987 | Goff et al. | |
| 4,665,903 A | 5/1987 | Whitehead | |
| 4,666,428 A | 5/1987 | Mattioli et al. | |
| 4,669,456 A | 6/1987 | Masters | |
| 4,671,261 A | 6/1987 | Fischell | |
| 4,682,583 A | 7/1987 | Burton et al. | |
| 4,682,589 A | 7/1987 | Finney | |
| 4,693,719 A | 9/1987 | Franko | |
| 4,699,128 A | 10/1987 | Hemmeter | |
| 4,718,410 A | 1/1988 | Hakky | |
| 4,724,830 A | 2/1988 | Fischell | |
| 4,726,360 A | 2/1988 | Trick et al. | |
| 4,730,607 A | 3/1988 | Fischell | |
| 4,766,889 A | 8/1988 | Trick et al. | |
| 4,773,403 A | 9/1988 | Daly | |
| 4,782,826 A | 11/1988 | Fogarty | |
| 4,790,298 A | 12/1988 | Trick | |
| 4,791,917 A | 12/1988 | Finney | |
| 4,807,608 A | 2/1989 | Levius | |
| 4,829,990 A | 5/1989 | Thuroff et al. | |
| 4,832,681 A | 5/1989 | Lenck | |
| 4,881,530 A | 11/1989 | Trick | |
| 4,881,531 A | 11/1989 | Timm et al. | |
| 4,895,139 A | 1/1990 | Hauschild et al. | |
| 4,899,737 A | 2/1990 | Lazarian | |
| 4,917,110 A | 4/1990 | Trick | |
| 4,988,357 A | 1/1991 | Koss | |
| 5,010,882 A | 4/1991 | Polyak et al. | |
| 5,048,510 A | 9/1991 | Hauschild et al. | |
| 5,050,592 A | 9/1991 | Olmedo | |
| 5,062,416 A | 11/1991 | Stucks | |
| 5,062,417 A | 11/1991 | Cowen | |
| 5,063,914 A | 11/1991 | Cowen | |
| 5,067,485 A | 11/1991 | Cowen | |
| 5,101,813 A | 4/1992 | Trick | |
| 5,112,295 A | 5/1992 | Zinner et al. | |
| 5,114,398 A | 5/1992 | Trick et al. | |
| 5,129,880 A | 7/1992 | Grundei | |
| 5,141,509 A | 8/1992 | Burton et al. | |
| 5,167,611 A | 12/1992 | Cowan | |
| 5,171,272 A | 12/1992 | Levius | |
| 5,176,708 A | 1/1993 | Frey et al. | |
| 5,250,020 A | 10/1993 | Bley | |
| 5,263,981 A | 11/1993 | Polyak et al. | |
| 5,283,390 A | 2/1994 | Hubis et al. | |
| 5,344,388 A | 9/1994 | Maxwell et al. | |
| 5,433,694 A | 7/1995 | Lim | |
| 5,445,594 A | 8/1995 | Elist | |
| 5,509,891 A | 4/1996 | DeRidder | |
| 5,512,033 A | 4/1996 | Westrum, Jr. et al. | |
| 5,553,379 A | 9/1996 | Westrum, Jr. et al. | |
| 5,669,870 A | 9/1997 | Elist | |
| 5,704,895 A | 1/1998 | Scott et al. | |
| 5,730,154 A | 3/1998 | DeRidder | |
| 5,851,176 A | 12/1998 | Willard | |
| 5,885,205 A | 3/1999 | Kassman | |
| 5,895,424 A | 4/1999 | Steele, Sr. et al. | |
| 5,899,849 A | 5/1999 | Elist | |
| 6,171,233 B1 | 1/2001 | Willard | |
| 6,346,492 B1 | 2/2002 | Koyfman | |
| 6,443,887 B1 | 9/2002 | Derus et al. | |
| 6,533,719 B2 | 3/2003 | Kuyava et al. | |
| 6,558,315 B1 | 5/2003 | Kuyava | |
| 6,579,230 B2 | 6/2003 | Yachia et al. | |
| 6,600,108 B1 | 7/2003 | Mydur et al. | |
| 6,723,042 B2 | 4/2004 | Almli et al. | |
| 6,730,017 B2 | 5/2004 | Henkel et al. | |
| 6,733,527 B2 | 5/2004 | Koyfman | |
| 6,929,599 B2 | 8/2005 | Westrum, Jr. | |
| 6,935,847 B2 | 8/2005 | Kuyava et al. | |
| 6,991,601 B2 | 1/2006 | Kuyava et al. | |
| 7,066,877 B2 | 6/2006 | Kuyava | |
| 7,066,878 B2 | 6/2006 | Eid | |
| 7,091,420 B2 * | 8/2006 | Lee | H01B 11/12 174/110 R |
| 7,169,103 B2 | 1/2007 | Ling et al. | |

(56) References Cited

U.S. PATENT DOCUMENTS

| | | |
|---|---|---|
| 7,244,227 B2 | 7/2007 | Morningstar |
| 7,250,026 B2 | 7/2007 | Kuyava |
| 7,350,538 B2 | 4/2008 | Kuyava et al. |
| 7,390,296 B2 | 6/2008 | Mische |
| 7,438,682 B2 | 10/2008 | Henkel et al. |
| 7,491,164 B2 | 2/2009 | Choi et al. |
| 7,637,861 B2 | 12/2009 | Kuyava et al. |
| 7,972,263 B2 | 7/2011 | Runyan |
| 8,911,350 B2 | 12/2014 | George et al. |
| 2002/0033564 A1 | 3/2002 | Koyfman |
| 2002/0082473 A1 | 6/2002 | Henkel et al. |
| 2002/0082709 A1 | 6/2002 | Almli et al. |
| 2002/0091302 A1 | 7/2002 | Kuyava et al. |
| 2003/0028076 A1 | 2/2003 | Kuyava et al. |
| 2004/0220447 A1 | 11/2004 | Morningstar |
| 2005/0014993 A1 | 1/2005 | Mische |
| 2006/0076156 A1* | 4/2006 | Lee .................... H01B 11/12 174/110 R |
| 2006/0235267 A1 | 10/2006 | George et al. |
| 2006/0289196 A1* | 12/2006 | Lee .................... H01B 11/12 174/110 R |
| 2008/0103353 A1 | 5/2008 | Jahns et al. |
| 2008/0114202 A1 | 5/2008 | Kuyava et al. |
| 2009/0105530 A1 | 4/2009 | Kuyava |
| 2009/0105818 A1 | 4/2009 | George et al. |
| 2009/0124851 A1 | 5/2009 | Kuyava |
| 2009/0287042 A1 | 11/2009 | Almli et al. |

FOREIGN PATENT DOCUMENTS

| | | |
|---|---|---|
| EP | 0065853 A1 | 12/1982 |
| EP | 0137752 | 8/1989 |
| EP | 0774935 | 7/1995 |
| EP | 0682923 A1 | 11/1995 |
| EP | 0925764 A1 | 6/1999 |
| GB | 2151484 | 7/1985 |
| GB | 2160777 | 1/1986 |
| GB | 2192546 | 1/1988 |
| WO | 8000302 A1 | 3/1980 |
| WO | 8500513 A1 | 2/1985 |
| WO | 8601398 | 3/1986 |
| WO | 9203107 A1 | 3/1992 |
| WO | 9404095 A1 | 3/1994 |
| WO | 9604865 | 2/1996 |
| WO | 02051339 A2 | 7/2002 |

OTHER PUBLICATIONS

Agrawal, V. et al., "An audit of implanted penile prostheses in the UK", BJU International 98, 293-295 (2006).

Akin-Olugbade, O. et al., "Determinants of Patient Satisfaction Following Penile Prosthesis Surgery", J Sex Med. 2006: 3: 743-48.

Al-Najar, A., et al., "Should being aged over 70 years hinder penile prosthesis implantation?", BJU International 2009 1-4.

AMS 700 CX Penile Prosthesis (Brochure) 2 pages 1999.

AMS 700 Inflatable Penile Prosthesis Product Line 45 pages (1992).

AMS (Brochure) 700 Series Tactile (Pump 2 pages) 2004.

AMS (Brochure) Ultrex/Ultrex Plus (10 Pages) (1998).

AMS Ambicor Penile Prosthesis (Brochure) 1996.

Merino, G. Atienza, "Penile Prosthesis for the treatment of erectile dysfunction" Actas Urol Esp. 2006; 30(2): 159-69.

Bella, A. et al., "Initial experience with 50 patients using the new AMS 700 with MS Pump Series inflatable penile prosthesis" Poster #44 J Sex Med., Jan. 2008;5 (suppl 1) p. 20.

Candela, J. et al., "Three-piece inflatable penile prosthesis implantation . . . " J La State Med Soc 148:296-301 (1996).

Daitch, J et al., "Long-Term Mechanical Reliability of AMS 700 Series Inflatable Penile Prostheses: Comparison . . . " J. Urol. 158: 1400-1402; Oct. 1997.

Delk, J. "Early Experience with the American Medical Systems New Tactile Pump: Results of a Multicenter Study" J Sex Med., 2005; 2:266-271.

Deuk Choi, Y. et al., "Mechanical Reliability of the AMS 700 CXM Inflatable Penile Prosthesis for the Treatment of Male Erectile Dysfuntion" J. Urol. 168, 822-824, Mar. 2001.

Deveci, S. et al., "Penile Length Alterations following Penile Prosthesis Surgery" European Urol. 51 (2007) 1128-31.

Durazi, M. et al., "Penile Prosthesis Implantation for Treatment of Postpriapism Erectile Dysfunction" Urol. J. 5(2) (2008) 115-19.

Eid, J., "What is new for inflatable penile prostheses?" Curr. Opin. Urol. 19:582-588 (2009).

Gefen, A. "Stresses in the normal and diabetic human penis following implantation of an inflatable prosthesis." Med. Biol. Eng. Comput., 1999, 37, 625-31.

Garber, B. "Inflatable penile prostheses for the treatment of erectile dysfunction." Exper Rev. Med. Devices 2(3), 341-50 (2005).

Gefen, A. et al., "A biomechanical model of Peyronie's disease" J. Biomech. 33 (2000) 1739-44.

Gefen, A. et al., "Optimization of Design and Surgical Positioning of Inflatable Penile Prostheses" Annals of Biomed. Eng. 28 (2000) 619-28.

Henry, G. et al., "Revision Washout Decreases Implant Capsule Tissue Culture Positivity: A Multicenter Study" J. Urol. vol. 179, 186-190, Jan. 2008.

Henry, G. "Historical Review of Penile Prosthesis Design and Surgical Techniques: Part 1 of a Three-Part Review Series on Penile Prosthetic Surgery" J. Sex Med. 2009; 6:675-681.

Henry, G. "Updates in inflatable Penile Prostheses" Urol Clin N Am 34 (2007) 535-547.

Hoebeke, P. et al., "Erectile Implants in Female-to-Male Transsexuals: Our Experience in 129 Patients" Eur. Urol. (2009), doi: 10.1016/j.eururo.2009.03.013.

InhibiZone Antibiotic Surface Treatment, (AMS Brochure) 4 pages 2001.

Kadioglu, A. et al., "Surgical Treatment of Peyronie's Disease: A Critical Analysis" European Urology 50 (2006) 235-248.

Kava, B. et al., "Efficacy and Patient Satisfaction Associated with Penile Prosthesis Revision Surgery" J. Sex Med. 2007; 4:509-518.

Leriche, A., Long-term outcome of forearm flee-lap phalloplasty in the treatment of transsexualism: BJU International 101: 1297-1300 (2008).

Levine, L. et al., "Mechanical Reliability and Safety of, and Patient Satisfaction with the Ambicor Inflatable Penile Prosthesis: Results of a 2 Center Study", J. Urol. vol. 166, 932-937, Sep. 2001.

Lumen, N. "Phalloplasty: A Valuable Treatment for Males with Penile Insufficiency", Urology 71(2), 2008 272-276.

Lux, M. et al., "Outcomes and Satisfaction Rates for the Redesigned 2-Piece Penile Prosthesis" J. Urol. vol. 177, 262-266, Jan. 2007.

"The Results Are in" Alpha I Setting High Standards for 3-piece Inflatable Implants Mentor Advertisement 15 pages.

Mentor New from Mentor Urology Alpha I Narrow-Base (Brochure) 2 pages 1996.

Mentor Alpha I Inflatable Penile Prosthesis (Brochure) 2 pages Jul. 1996.

Mentor Surgical Protocol Alpha I Inflatable Penile Prosthesis 17 pages May 1998.

Mentor Patient Guide for Alpha I Inflatable Penile Implant (Brochure) 2 pages 1997.

Mulcahy, J. "Distal Corporoplasty for Lateral Extrusion of Penile Prosthesis Cylinders" J. Urol. vol. 161, 193-195 Jan. 1999.

Murphy, AM. et al., "Failure of the Ambicors inflatable penile prosthesis to deflate" International Journal of Impotence Research (2005) 17. 291-292.

Nahrstadt, BC. et al. "Informed consent for penile prosthesis", International Journal of Impotence Research (2009) 21, 37-50.

"Parylene Micro Coating" AMS Brochure, 4 pages 2000.

Sadeghi-Nejad, H. "Penile Prosthesis Surgery: A Review of Prosthetic Devices and Associated Complications" J. Sex Med. 2007; 4:296-309.

Scarzella, IG. et al., "Use of Ambicor Penile Prosthesis in Peyronie's Disease and as Replacement for Malfunctioning AMS 700 Devices", J. Sex Med. 2004; Suppl. 1.

Simmons, M. et al., "Penile prosthesis implantation: past, present and future", International Journal of Impotence Research (2008) 20, 437-444.

(56) References Cited

OTHER PUBLICATIONS

Ultrex Plus Penile Prosthesis (AMS Advertisement) 1 page (1992).
Wang, Shyh-Jen et al., "Hardness evaluation of penile prostheses", International Journal of Urology (2006) 13, 569-572.
Mentor Surgical Protocol Alpha I Inflatable Penile Prosthesis 15 pages 1998.
Mentor Urology Products, (Brochure), Mentor, 20 pages (1998).
Hellstrom, WJG "Three-piece inflatable penile prosthesis components (surgical pearls on reservoirs, pumps, and rear-tip extenders)", International Journal of Impotence Research (2003) 15, Suppl 5, S136-S138.
Kim, Sae-Chui, "Mechanical Reliability of AMS Hydraulic Penile Prostheses" J. of Korean Med. Sci. 10(6); 422-425, Dec. 1995.
Mooreville, M. et al., "Implantation of Inflatable Penile Prosthesis in Patients with Severe Corporeal Fibrosis: Intraoduction of a New Penile Cavernotome", J. Urol. 162, 2054-2057, Dec. 1999.
Montague, DK "Early Experience with the Controlled Girth and Length Expanding Cylinder of the American Medical Systems Ultrex Penile Prosthesis", J. Urol. 148; 1444-1446, Nov. 1992.
Montague, DK "Cylinder Sizing: less is more", International Journal of Impotence Research (2003) 15, Suppl 5, S132-S133.
Montague, DK et al., "Future considerations: advances in the surgical management of erectile dysfunction", International J. Impotence Res. (200) 12, Suppl 4, S140-S143.
Montague, DK et al., "AMS 3-Piece Inflatable Penile Prosthesis Implantation in Men with Peyronie's Disease: Comparison of Cx and Ultrex Cylinders" J. Urol. 156, 1633-1635, Nov. 1996.
Montague, DK et al., "Penile Prosthesis Infections" International Journal of Impotence Research (2001) 13, 326-328.
Malloy, T. et al., "Imporved Mechanical Survival with Revised Model Inflatable Penile Prosthesis Using Rear-Tip Extenders", J. Urol. 128 Sep. 1982, 489-491.
Chang, Yao-Jen et al., "Penile Prosthesis Implantation" eMedicine http://www.emedicine.com/med/topic3047.htm 19 pages (2003).
Gregory, J., et al., "The Inflatable Penile Prosthesis: Failure of the Rear Tip Extender in Reducing the Incidence of Cylinder Leakage" J. Urol. vol. 131 668-669 (1984).
Joseph, D. et al., "Bilateral Dislocation of Rear Tip Extenders fro the Inflatable Penile Prosthesis" J. Urol. vol. 128, Dec. 192 1317-1318.
Prosecution History from corresponding U.S. Appl. No. 12/256,829 including: Notice of Allowance mailed Sep. 5, 2014; Non-Final Office Action mailed Apr. 22, 2014; Final Office Action mailed Sep. 22, 2010; and Non-Final Office Action mailed Apr. 19, 2010.
Acu-Form Penile Prosthesis, Mentor, 1 page Aug. 1997.
Agrawal, Wineet et al., An Audit of Implanted Penile Prostheses in the UK, BJU International pp. 393-395 (2006).
Akand, Murat, Mechanical Failure With Malleable Penile Prosthesis, J. Urol. 70:1007 e11-1007. e12 (2007).
AMS Malleable 600 TM American Medical Systems Publication 30915, 1983.
Anafarta, Kadri, Clinical Experience with Inflatable and Malleable Penile Implants in 104 Patients, Urol. Int. 56:100-104 (1996).
Benson RC Jr., Patterson DE, Barrett DM, Long-term results with the Jonas malleable penile prosthesis. J. Urol. 195 Nov; 134(5):899-901.
Burns-Cox, N., Fifteen Years Experience of Penile Prosthesis Insertion, International J. Impotence Res. (1997) 9, 211-216.
Chiang, Han-Sun, 10 Years Experience with Penile Prosthesis Implantation in Taiwanese Patients, J. Urol. vol. 163:476-480 (2000).
Choi, Hyung Ki, Ten Years of Experience with Various Penile Prosthesis in Korean, Yasei Medical J. vol. 35, No. 2 (1994) 209-217.
Dorflinger T, Bruskewitz R, AMS Malleable Penile Prosthesis, Urology, Dec. 1986; 28(6):480-5.
Fathy, Ahmad, Experience with Tube (Promedon_Malleable Penile Implant, Urol. Int. 2007; 79:244-247.
Ferguson, Kenneth, Prospective Long-Term Results and Quality-of-Life-Assessment After Dura-II Penile Prosthesis Placement, Urol. 61(2) 437-441 (2003).
Fogarty, JD, Cutaneous Temperature Measurements in Men with Penile Prosthesis: A Comparison Study, Int. J. of Impotence Res. (2005) 17,506-509.
Jonas U. Silicone-Silver Penis Prosthesis (Jonas-Eska), Long-Term Reconstruction. J. Urol. Sep. 1998; 160(3 Pt 2):1164-8.
Kardar, A.H., An Unusual Complication of Penile Prosthesis Following Urethroplasty, Scand. J. Urol. Nephrol. 36: 89-90, 2002.
Kaufman, JJ, Raz S. Use of Implantable Prostheses for the Treatment of Urinary Incontinence and Impotence, Am J Surg. Aug. 1975; 130(2):244-50.
Khoudary, Kevin, Design Considerations in Penile Prostheses: The American Medical Systems Product Line, J. Long-Term Effects of Medical Implants, 7(1):55-64 (1997).
Krauss, Dennis J., Use of the Malleable Penile Prosthesis in the Treatment of Erectile Dysfunction: A Prospective Study of Postoperative . . . , J. Urol. vol. 142: 988-991 (1989).
Montague, Drogo, Surgical Approaches for Penile Prostheses Implantation: Penoscrotal VS Infrapubic, International J. Impotence Res. (2003) 15, Suppl. 5, S134-S135.
Morey, Allen et al., Immediate Insertion of a Semirigid Penile Prosthesis for Refractory Ischemic Priapism, Military Medicine, 172, 11:1211, 2007.
Mulcahy, John, Another Look at the Role of Penile Prostheses in the Management of Impotence, Urology Annual 11, pp. 169-185 (1997).
Parulkar, B.G., Revision Surgery for Penile Implants, Int. J. Impotence res. (1994) 6, 17-23.
Pearman, Ro, Insertion of a Silastic Penile Prosthesis for the Treatment of Organic Sexual Impotence. J. Urol. May 1972; 107(5):802-6.
Randrup, Eduardo, Penile Implant Surgery: Rear Tip Extender That Stays Behind, Urology 1992 34, 1 p. 87.
Rhee, Eugene, Technique for Concomitant Implantation of the Penile Prosthesis with the Male Sling. J. Urol. 173:925-927 (2006).
Salama, Nadar, Satisfaction with the Malleable Penile Prosthesis Among Couples from the Middle East: Is it Different . . . , Int. J. Impotence Res. 16:175-180 (2004).
Small, Michael, Small0Carr on Penile Prosthesis: A Report on 160 Cases and Review of the Literature. J. Urol. vol. 167. 2357-2360.
Smith, Christopher, Management of Impending Penile Prosthesis Erosion with a Polytetrafluoroethylene Distal Wind Sock Graft, J. Urol. vol. 160: 2037-2040, (1998).
Maul, Judd, Experience with the AMS 600 Malleable Penile Prosthesis, J. Urol. 135:929-931 (1986).
Mentor Urology Products, 18 pages, May (1998).
Merino, G. Atienza, Penile Prosthesis for the Treatment of Erectile Dysfunction, Actas Urol. Esp. 2006: 30(2): 159-169.
Minervini, Andrea, Outcome of Penile Prosthesis Implantation for Treating Erectile Dysfunction: Experience with 504 Procedures, BJU International 97:129-133, (2005).
Montague, Drogo, Clinical Guidelines Panel on Erectile Dysfunction: Summary Report on the Treatment of Organic Erectile Dysfunction, J. Urol. 156:2007-2011 (1996).
Montague, Drogo, Contemporary Aspects of Penile Prosthesis Implantation, Urol. Int. 2003: 70:141-146.
Montague, Drogo, Current Status of Penile Prosthesis Implantation, Urology Reports 2000, 1: 291-296.
Montague, Drogo, Experience with Semirigid Rod and Inflatable Penile Prostheses, J. Urol. 129:967-968, 1983.
Montague, Drogo, Penile Prosthesis Implantation, 712-719, 1994.
Montague, Drogo, Penile Prosthesis Implantation for End-Stage Erectile Dysfunction After Radical Prostatectomy, Reviews in Urol. vol. 7 Suppl. 2 S51-S57, 2005.
Kimoto, Y. et al., JSSM Guidelines for Erectile Dysfunction, Int. J. Urol (2008) 15, 564-76.
Natali, a. et al., Penile Implantation in Europe: Successes and Complications with W53 Implants in Italy and Germany, J. Sex. Med. 2008;5:1503-12.

(56) References Cited

OTHER PUBLICATIONS

Stein, Avi et al., Malleable Penile Prosthesis Removal Leaving Behind the Rear Tip Extenders: A Clinical Presentation, Urol. Int. 50:119-120 (1993).
Surgical Protocol, Mentor 5 pages Sep. 1997.
The AMS Hydroflex Self-Contained Penile Prosthesis, American Medical Systems Publication 50513 (1985).
Y00 JJ, Lee I, Atala A. Cartilage Rods as a Potential Material for Penile Reconstruction, J. Urol. Sep. 1998; 160(3 Pt 2): 1164-8; discussion 1178.
Zerman, Dirk-Henrik et al., Penile Prosthetic Surgery in Neurologically Impaired Patients: Long-Term Follow-Up, J. Urol. 175:1041-1044 (2006).

* cited by examiner

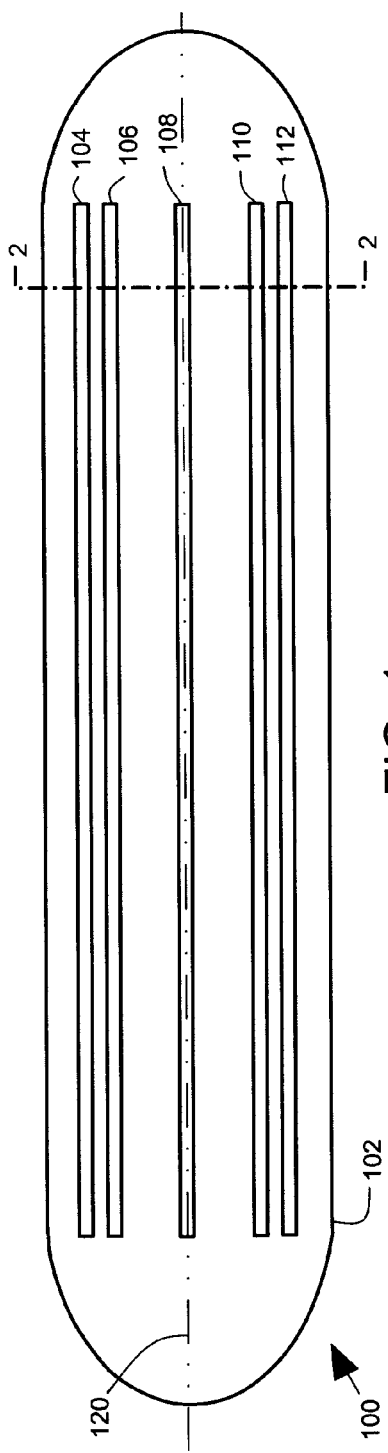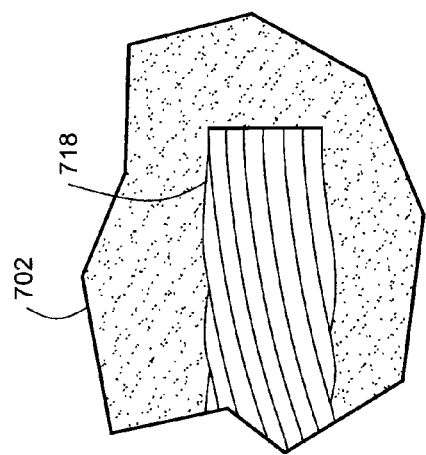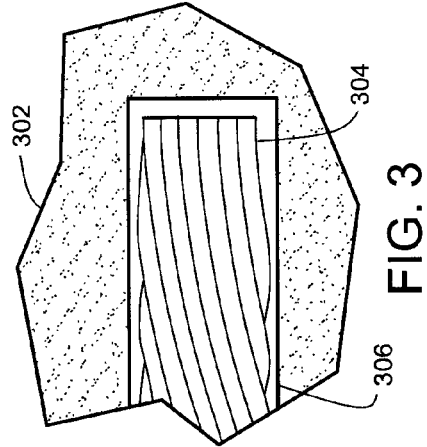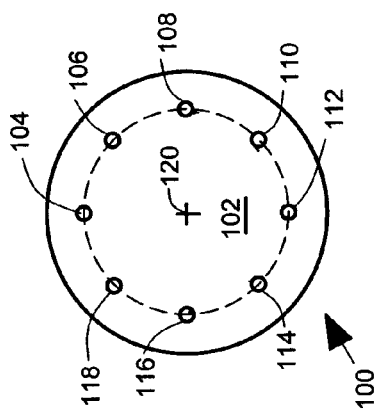
FIG. 1
FIG. 2
FIG. 3
FIG. 4

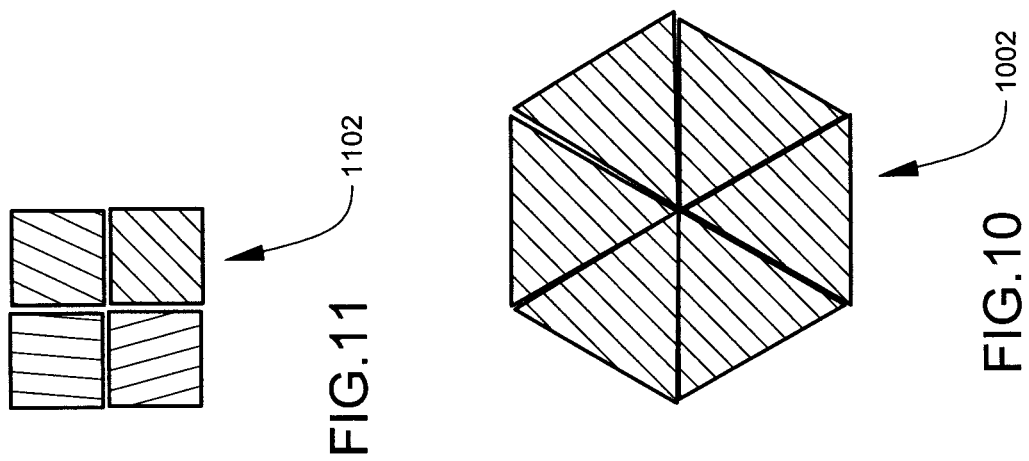
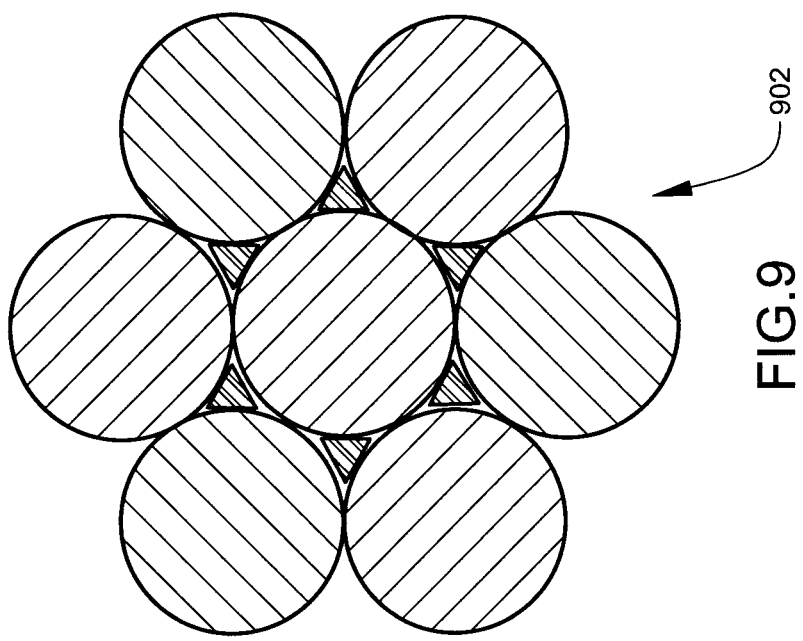

MALLEABLE PROSTHESIS WITH ENHANCED CONCEALABILITY

CROSS REFERENCE TO RELATED APPLICATIONS

This application is a continuation of U.S. patent application Ser. No. 12/256,829, filed Oct. 23, 2008, now U.S. Pat. No. 8,911,350, which claims the benefit of U.S. Provisional Patent Application Ser. No. 60/981,844, filed Oct. 23, 2007. The content of each of the above-identified applications is hereby incorporated by reference in its entirety.

FIELD OF THE INVENTION

The invention relates to implantable prosthetic devices. In particular, but not by way of limitation, the invention relates to implantable malleable (non-inflatable) penile prostheses.

BACKGROUND OF THE INVENTION

There are many causes of male impotence including those that are psychologically based as well as trauma related impotence. Procedures have been developed for treating impotence, and one such procedure involves the implantation of a penile prosthesis. There are two general types of penile implants, namely, the inflatable penile implant and the noninflatable penile implant. The noninflatable implants include those which incorporate a rigid rod and are permanently stiff and those formed of malleable or bendable materials and which may be bent between the erect and nonerect positions. U.S. Pat. No. 3,893,456 discloses a rigid rod type of penile prosthesis. Examples of malleable implants are shown in U.S. Pat. No. 3,987,789 and U.S. Pat. No. 4,151,841. One of the problems involved in malleable penile implants is the difficulty in concealing the device by positioning the rods in a bent configuration and remaining in that concealed position. This difficulty is often due to the large diameter of the rod. This difficulty is addressed by the malleable rod of the present invention wherein changes in the configuration of the rod provides greater positionability and concealability.

SUMMARY OF THE INVENTION

Embodiments of the invention are directed to a malleable penile prosthetic device for implantation within a penis of a user. In some embodiments, the malleable penile prosthetic device includes a columnar body and a plurality of malleable cores within the columnar body. The columnar body has a proximal end, a distal end, and a central axis extending from the proximal end to the distal end. Each of the plurality of malleable cores extends along the central axis, is angularly displaced about the central axis from neighboring malleable cores, and includes a bundle of wires surrounded by a sleeve.

BRIEF DESCRIPTION OF THE DRAWINGS

FIGS. 1 and 2 illustrate a prosthetic device.
FIGS. 3-8 illustrate bundles of wires in columns of resilient material.
FIGS. 9-11 illustrate examples of wire cross sections.

DETAILED DESCRIPTION OF ILLUSTRATIVE EMBODIMENTS

Figure 7:
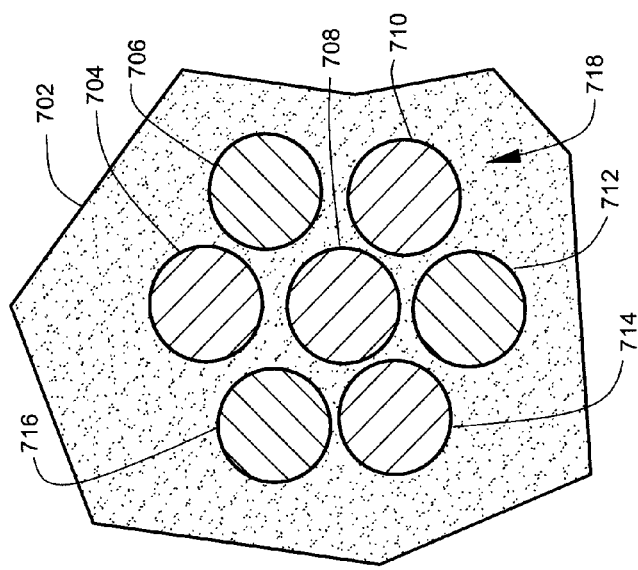
Figure 6:
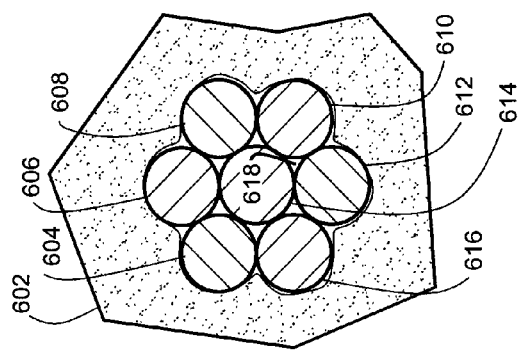
Figure 8:
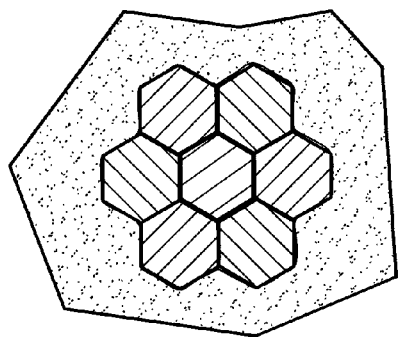
Figure 5:
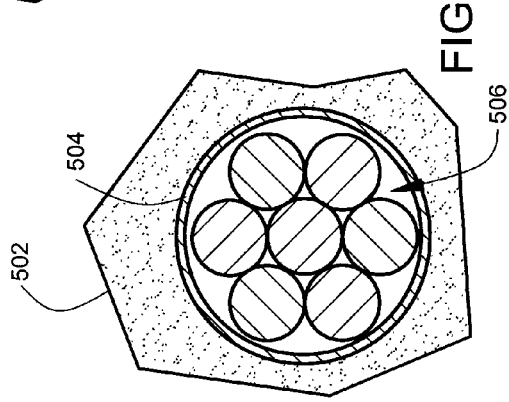

FIG. 1 illustrates a prosthetic device 100, and FIG. 2 illustrates a cross-sectional view (along line 2-2 in FIG. 1) of the prosthetic device 100. The prosthetic device 100 comprises a column 102 formed of resilient material. The resilient material can comprise silicone or other known biocompatible resilient prosthesis material. The prosthetic device 100 comprises multiple malleable cores 104, 106, 108, 110, 112, 114, 116 118 arranged inside the column 102. The multiple malleable cores 104, 106, 108, 110, 112, 114, 116, 118 are spaced apart from one another, spaced apart from a central axis 120, and positioned adjacent an outer diameter of the column 102. In one embodiment, the multiple malleable cores 104, 106, 108, 110, 112, 114, 116, 118 are positioned in a circular pattern at equally spaced intervals as illustrated. In the embodiment shown in FIGS. 1-2, eight malleable cores are illustrated, however, other numbers of cores in a range of 3 to 9 cores are also contemplated. Each of the multiple malleable cores 104, 106, 108, 110, 112, 114, 116 118 comprises a bundle of wires as illustrated in FIGS. 3-11. In one embodiment, the wires comprise metal alloy wires formed of a malleable material. The wires can be round wires, as illustrated in FIGS. 5-7, or the wires can have an approximately hexagonal cross section (FIG. 8), fitting together with one another to substantially eliminate void spaces between wires in the bundles. Other cross-sectional shapes of wires that reduce voids between wires, including triangles (1002 in FIG. 10) and squares (1102 in FIG. 11), are also contemplated. Combinations of smaller wires fitting into voids between larger wires (902 in FIG. 9) are also contemplated. Stainless steel or other known biocompatible metal alloy wires can be used. Individual wires, or wire bundles, can be covered with braided yarn, Teflon tubing or other jacketing material to enhance mechanical characteristics.

In one embodiment, the column 102 has a central hollow core (not illustrated) that is free of elastomer. The central hollow core reduces springback. The term "springback" refers to the amount of a return movement of a bent column after a bending force is removed. Springback causes a column that is bent into a position (either a straight or bent position) to lose part of the bend after the column is released. Springback is an undesirable property that adversely affects concealability. Springback requires the user to learn to bend the column past a desired position in order for it to have the desired position after springback, or requires the user to bend the column multiple times in order to obtain a concealed position. Springback is believed to be due to the shape and elastic recovery properties of materials in the column 102, and is reduced by providing the hollow core.

As illustrated in FIG. 3, a column 302 of resilient material can be cast, molded, drilled or otherwise shaped to have multiple hollow cavities 306 into which are later inserted bundles 304 of malleable wires. In one process, the resilient material is cooled to a low enough temperature to reduce resiliency and permit drilling of the material.

As illustrated in an embodiment shown in FIGS. 4 and 7, a column 702 of resilient material can fill intermediate spaces between wires 704, 706, 708, 710, 712, 714, 716 in a bundle 718. In one manufacturing process, resilient material is injected into a mold from which air has been evacuated so that the resilient material easily flows into and substantially fills intermediate spaces between the wires 704, 706, 708, 710, 712, 714, 716 in the bundle 718 as illustrated in FIG. 7.

As illustrated in FIG. 5, a column of resilient material 502 is applied around a jacket 504. The jacket 504 surrounds a bundle 506 of malleable wires. In one embodiment, the jacket 504 comprises plastic resin tubing. In another embodiment, the jacket 504 comprises heat shrink tubing. In one process, the jacket 504 resists flow of the liquid resilient material into the bundle 506 during curing. In one embodiment the jacket 504 functions as a slip surface that reduces drag on the bundle 506 as it bends.

As illustrated in FIG. 6, a column 602 of resilient material is applied around a bundle of wires 602, 604, 606, 608, 610, 612, 614, 616, leaving void spaces (such as void space 618) between wires in the bundle that are not filled with resilient material. In one process, the void spaces are left filled with trapped air or inert gas while the column of material 602 is introduced in a viscous liquid state and then cures into a resilient state around the outside of the bundle of wires.

The penile prostheses disclosed in FIGS. 1-11 are more easily concealed and have improved rigidity (resisting buckling of the column) relative to comparable existing devices. Bending rigidity refers to the ability of a column in a straight position to remain in a straight position when subjected to radial deflection forces (bending forces) encountered during intromission. The prostheses have a desired high level of rigidity to resist bending forces in a range of smaller bending forces encountered during intromission, but also respond by bending when subjected to a range of higher bending forces encountered when the user is intentionally bending the prosthesis. The penile prostheses disclosed in FIGS. 1-11 have improved axial rigidity, in other words, resistance to buckling when a compressive load force is applied that is aligned with the axis of the prosthesis.

The malleable type penile prosthesis includes a core of multiple bundles of malleable stainless steel wire. The bundles are generally aligned with the prosthesis major axis but, instead of being in the center of the prosthesis, they are positioned radially displaced from the center, and are arranged proximate to a lengthwise side of the prosthesis. Each of the bundles comprises strands of wire wrapped around each other. A relatively small number of wires is used in each bundle. Each bundle typically includes a smaller number of wires than would be found in an axial bundle of a conventional prosthesis, and the enhanced malleability feature of the prosthesis is derived from smaller contributions of malleability from each of the bundles with smaller numbers of wires per bundle.

In one embodiment, the individual wires in the bundles are individually encased in silicone elastomer. In another embodiment, each bundle of wires is covered by a sleeve so that there is little or no elastomer in the spaces between wires in a bundle. Another variation would have no elastomer inside, just a sleeve covering the device with the wire bundles loose inside. In yet another embodiment, the wire bundles are inserted into cavities or pockets of a previously cured elastomer body, so that the bundles are free to move in the pockets, unrestrained by bonding to the elastomer body.

The outer configuration of the prosthesis can be the same as the outer configuration of conventional malleable prostheses, and known methods of implantation can be used. The wire bundles are spaced radially from the prosthesis center axis, and this outward position imparts to the prosthesis a greater resistance to bending when subjected to an externally applied turning moment (torque). The prosthesis is less susceptible to undesired bending when exposed to inadvertent low level turning moments. Because the individual bundles consist of fewer strands of wire, the bundles are more malleable and have reduced springback (elastic recovery) when the prosthesis is bent for concealment. The lower springback means the prosthesis maintains its bend and provides enhanced concealability relative to conventional prostheses.

Also contemplated is an embodiment without silicone elastomer in the center or adjacent the wire bundles. Such an embodiment would springback less when bent because there is less elastomer to provide the force to spring back, and the wire bundles would be free to bend with a larger radius, which larger radius would inherently have lower springback force.

Although the present invention has been described with reference to preferred embodiments, workers skilled in the art will recognize that changes may be made in form and detail without departing from the spirit and scope of the invention.

What is claimed is:

1. A malleable penile prosthetic device for implantation within a penis of a user, the device comprising:
    a columnar body having a proximal end, a distal end, and a central axis extending from the proximal end to the distal end, the columnar body including a resilient material that extends from the proximal end to the distal end; and
    a plurality of malleable cores that are wholly enclosed within the columnar body, each malleable core:
        being elongate;
        being angularly displaced about the central axis from neighboring malleable cores; and
        including a bundle of wires that define at least one void space between wires of the bundle of wires, surfaces of wires of the bundle of wires defining an outside of the bundle of wires being in direct contact with the resilient material, each wire of the bundle of wires having a longitudinal axis extending along the central axis,
    wherein the malleable penile prosthetic device is:
        when placed in a straight position, sufficiently rigid to remain in the straight position during intromission; and
        when placed in a bent position, sufficiently malleable to remain in the bent position, wherein the central axis of the columnar body does not extend through a malleable core.

2. The device according to claim 1, wherein the malleable cores are each positioned closer to an outer wall of the columnar body than the central axis.

3. The device according to claim 1, wherein the malleable cores are displaced from each other at equally spaced angular gaps about the central axis.

4. The device according to claim 3, wherein the malleable cores are positioned in a circular pattern around the central axis.

5. The device according to claim 1, wherein the wires of the bundle of wires of at least one malleable core have a circular cross-sectional shape.

6. The device according to claim 1, wherein the wires of the bundle of wires of at least one malleable core have cross-sectional shapes that reduce a size of the at least one void space of the at least one malleable core relative to void space between equally sized wires of the at least one malleable core having a circular cross-sectional shape.

7. The device according to claim 1, wherein the resilient material extends between neighboring malleable cores.

8. The device according to claim 1, wherein the at least one void space of at least one malleable core is filled with trapped air.

9. The device according to claim 1, wherein the at least one void space of at least one malleable core is filled with an inert gas.

10. The device according to claim 1, wherein the wires of the bundle of wires of at least one malleable core are wires having a first cross-sectional shape, the bundle of wires of the at least one malleable core further including a wire having a second cross-sectional shape that is disposed in the at least one void space of the at least one malleable core, the second cross-sectional shape being different than the first cross-sectional shape.

11. A malleable penile prosthetic device for implantation within a penis of a user, the device comprising:
 a columnar body having a proximal end, a distal end, and a central axis extending from the proximal end to the distal end, the columnar body including a resilient material that extends from the proximal end to the distal end; and
 a plurality of malleable cores that are wholly enclosed within the columnar body, each malleable core:
  being elongate;
  being angularly displaced about the central axis from neighboring malleable cores;
  spaced from the central axis; and
  including a bundle of wires that define at least one void space between wires of the bundle of wires, surfaces of wires of the bundle of wires defining an outside of the bundle of wires being in direct contact with the resilient material, each wire of the bundle of wires having a longitudinal axis extending along the central axis,
 wherein the malleable penile prosthetic device is:
  when placed in a straight position, sufficiently rigid to remain in the straight position during intromission; and
  when placed in a bent position, sufficiently malleable to remain in the bent position.

* * * * *